United States Patent
Rosales et al.

(10) Patent No.: US 7,840,511 B2
(45) Date of Patent: Nov. 23, 2010

(54) LEARNING OR INFERRING MEDICAL CONCEPTS FROM MEDICAL TRANSCRIPTS USING PROBABILISTIC MODELS WITH WORDS OR PHRASES IDENTIFICATION

(75) Inventors: Romer E. Rosales, Downingtown, PA (US); Praveen Krishnamurthy, Mountain View, CA (US); R. Bharat Rao, Berwyn, PA (US); Harald Steck, Phoenixville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 685 days.

(21) Appl. No.: 11/850,193

(22) Filed: Sep. 5, 2007

(65) Prior Publication Data
US 2008/0059391 A1    Mar. 6, 2008

Related U.S. Application Data

(60) Provisional application No. 60/842,457, filed on Sep. 6, 2006.

(51) Int. Cl.
*G06N 5/00* (2006.01)
(52) U.S. Cl. ...................................................... 706/45
(58) Field of Classification Search ................... 706/45
See application file for complete search history.

(56) References Cited

U.S. PATENT DOCUMENTS

| 2003/0093003 | A1* | 5/2003 | Watrous et al. ............. 600/528 |
| 2003/0120458 | A1 | 6/2003 | Rao et al. |
| 2003/0125984 | A1 | 7/2003 | Rao et al. |
| 2003/0125985 | A1 | 7/2003 | Rao et al. |
| 2003/0130871 | A1 | 7/2003 | Rao et al. |
| 2004/0172297 | A1 | 9/2004 | Rao et al. |
| 2006/0265253 | A1 | 11/2006 | Rao et al. |

OTHER PUBLICATIONS

Taskar et al. "Discriminative Probabilistic Models for Relation Data", UAI, 2002, 8 pages.*

* cited by examiner

*Primary Examiner*—Michael B. Holmes
*Assistant Examiner*—Li-Wu Chang
(74) *Attorney, Agent, or Firm*—Joshua Ryan

(57) ABSTRACT

A medical concept is learned about or inferred from a medical transcript. A probabilistic model is trained from medical transcripts. For example, the problem is treated as a graphical model. Discriminative or generative learning is used to train the probabilistic model. A mutual information criterion can be employed to identify a discrete set of words or phrases to be used in the probabilistic model. The model is based on the types of medical transcripts, focusing on this source of data to output the most probable state of a patient in the medical field or domain. The learned model may be used to infer a state of a medical concept for a patient.

15 Claims, 3 Drawing Sheets

LEARNING OR INFERRING MEDICAL CONCEPTS FROM MEDICAL TRANSCRIPTS USING PROBABILISTIC MODELS WITH WORDS OR PHRASES IDENTIFICATION

RELATED APPLICATIONS

The present patent document claims the benefit of the filing date under 35 U.S.C.§119(e) of Provisional U.S. Patent Application Ser. No. 60/842,457, filed Sep. 6, 2006, which is hereby incorporated by reference.

BACKGROUND

The present embodiments relate to determining the state of a patient from medical transcripts. Medical transcripts are a prevalent source of information for analyzing and understanding the state of patients. Medical transcripts are stored as text in various forms. Natural language is a common form. The terminology used in the medical transcripts varies from patient-to-patient due to difference in medical practice. The variation and use of medical terminology requires a trained or skilled medical practitioner to understand the medical concept relayed by a given transcript, such as indicating a patient has had a heart attack.

Automated analysis is difficult. The unstructured nature of the text and the various ways used to refer to the same medical condition (e.g., disease, event, symptom, billing code, or standard label) make automated analysis challenging. One approach is phrase spotting, such as searching for specific key terms in the medical transcript. The existence of a word or words is used to show the existence of the state of the patient. The existence of the word or words may be used with other information to infer a state, such as disclosed in U.S. Published Application No. 2003/0120458. Rules are used to determine the contribution of any identified word to the overall inference. Certain conditions may be only implied through a reference to related symptoms or diseases and never mentioned explicitly. The mere presence or absence of certain phrases or words immediately associated to the condition may not be enough to infer the condition of patients with high certainty.

SUMMARY

In various embodiments, systems, methods, instructions, and computer readable media are provided for learning about or inferring a medical concept from a medical transcript. A probabilistic model is trained or learned from medical transcripts. For example, the problem is treated as a graphical model. Discriminative or generative learning is used to train the probabilistic model. In order to identify a discrete set of words or phrases to be used in the probabilistic model, the mutual information criterion can be employed. The set is identified from training data, containing labeled text passages. The same or different labeled text passages are used to train the probabilistic model. The model is based on the types of medical transcripts, focusing on this source of data to output the most probable state of a patient in the medical field or domain. The learned model may be used to infer a state (e.g., yes or no) of a medical concept (e.g., heart attack) for a patient.

In a first aspect, a system is provided for inferring a medical concept from a medical transcript. An input is operable to receive user identification of the medical transcript. A processor is operable to receive a text passage from the medical transcript and operable to apply a probabilistic model to the text passage of the medical transcript. A display is operable to output a state associated with a patient. The state is inferred as a function of an output from the probabilistic model applied to the text passage.

In a second aspect, a computer readable storage medium has stored therein data representing instructions executable by a programmed processor for inferring a medical concept from a medical transcript. The instructions include applying a probabilistic model to the medical transcript of a patient, the probabilistic model probabilistically associating different words of the medical transcript to a state of the medical concept, and outputting the state as indicated by the medical transcript of the medical concept as a function of the probabilistic associations of the different words to the state.

In a third aspect, a method is provided for learning about a medical concept from a medical transcript. A plurality of labeled text passages from medical transcripts is received. A processor constructs a probabilistic model of the medical concept as a function of the labeled text passages of the medical transcripts. The probabilistic model is output.

Any one or more of the aspects described above may be used alone or in combination. These and other aspects, features and advantages will become apparent from the following detailed description, which is to be read in connection with the accompanying drawings. The present invention is defined by the following claims, and nothing in this section should be taken as a limitation on those claims. Further aspects and advantages are discussed below in conjunction with the preferred embodiments and may be later claimed independently or in combination.

DESCRIPTION OF EMBODIMENTS

Figure 1:
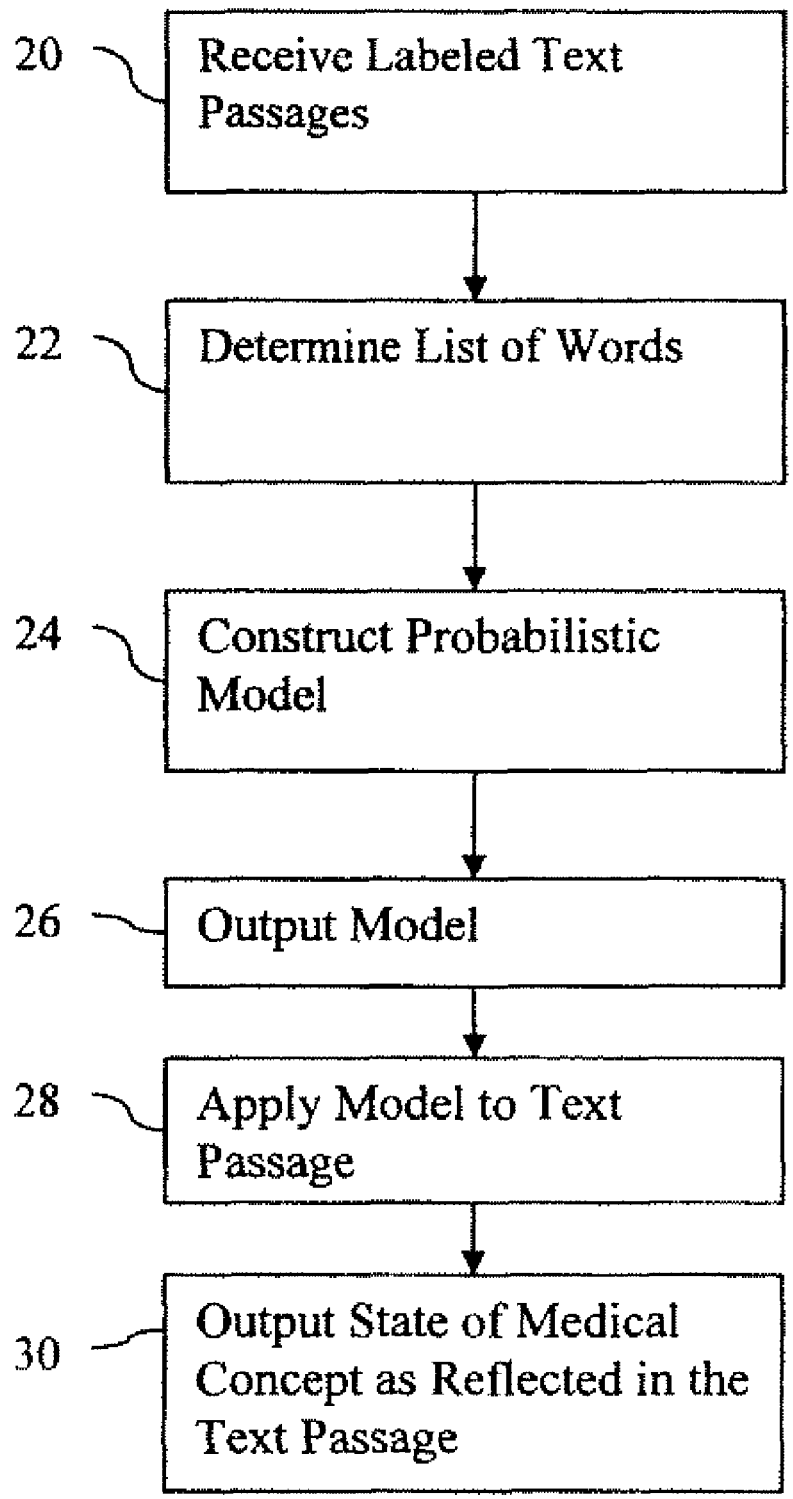
FIG. 1 is a flow chart diagram of one embodiment of a method for learning about and for inferring a medical concept from a medical transcript.

Based on probabilistic modeling and reasoning, electronic medical transcripts are automatically mined or explored for high-level information about the patient's medical state (disease, condition, symptoms, test results, other events, etc.). For example, whether a patient has a particular medical condition is discovered with a processor from text found in the doctor's notes. In general, this form of high-level information may not be directly available, but is latent in the patient data. It may be very costly and difficult to obtain due to labor expense of hiring a medical professional to review the data. Instead, a processor makes available information to enhance clinical decision support. For example, for a medical concept such as 'heart failure,' the processor automatically determines the odds that heart failure has indeed occurred or not occurred in the given patient based on a transcribed text passage. In this example, the concept is 'heart failure' and the states are 'occurred' and 'not occurred.'

A probabilistic methodology is used to infer the state of the patient. A probabilistic model takes into account the statistics of words or words and their relationship to patient states and conditions. There are many variables, some known and others unknown, that can influence the meaning of a sentence, and their relationship and combined effect is clearly not deterministic. Medical concepts cannot be easily inferred from words or phrases alone, such as in phrase spotting, since the language employed is usually complex and unstructured from a computational perspective.

Two general tasks are provided in a same or different method and/or system. In the first task, a probabilistic model of medical concepts is constructed from labeled and/or unlabeled text passages. These text passages and the resulting model are generally for large populations and are not patient specific. By modeling just or based on the medical transcripts without other inputs, the diagnostic input from medical professionals closest to the situation may be determined with a processor.

To construct or learn a probabilistic model using a graphical model approach, available data (e.g., existing records) are used to determine the variables of interest, determine their conditional independencies, and calculate the conditional probability function of each node given the state of its parent node(s). Labeled data is input for model construction. The probabilistic model can be constructed from labeled text passages at various levels, such as at a sentence level, document level, or patient level. The labeled text passages are known to refer to or posses a particular state for specific medical concept concepts. Unlabeled data may be used, such as in active learning by a previously trained model. For unlabeled text passages, the state of the medical concept of interest is unknown.

In the second task, the probabilistic model determines a probability distribution for the different states related to one or more medical concepts, given patient specific medical evidence (e.g., one or more medical text passages). The probabilistic model is specific to medical text passages and may be specific to medical fields or concepts, more likely providing more specific and sensitive indication of relevance of a medical transcript to the patient state. The probabilistic model determines probabilities over concepts given evidence. A posteriori probabilities are inferred over concepts conditioned on the gathered evidence.

Constructing and applying the probabilistic model specific to medical text passages or transcripts may provide different benefits. Early detection of disease conditions may be provided by thorough or relatively inexpensive automated checking. A second opinion based on the notes or other free text is provided. More efficient utilization of the information available in the patient electronic medical record (EMR) may be provided. The amount of manual, time-consuming record inspection may be reduced. The need of expert knowledge provided directly from medical specialists may be reduced. Prompt analysis of a large amount of clinical data may be provided. Estimation and evaluation of quality of care measures (for example, guideline compliance) may be automated. Rapid exploration of large patient populations (for example, for trial recruitment) may be provided.

FIG. 1 shows one embodiment of a method for learning about and inferring a medical concept from a medical transcript. The method is implemented with the system of FIG. 4 or a different system. The acts are performed in the order shown or a different order. Additional, different, or fewer acts may be provided. For example, acts 20-26 are performed without acts 28-30 or vice versa. As another example, act 22 is not performed or a list is input manually rather than automatically determined.

In act 20, a plurality of labeled text passages from medical transcripts are received. The medical transcripts are unstructured, natural language information from a medical professional. For example, free text is provided. The text passages may be formatted pursuant to a word processing program, but are not data entered in predefined fields, such as a spreadsheet or other data structure. Instead, the text passages represent words, phrases, sentences, documents, collections thereof or other free-form text.

The text passages are from a medical professional, such as a physician, lab technician, imaging technician, nurse, medical facility administrator or other medical professional. The text passages include medical related information, such as comments relevant to diagnosis of a patient or person being examined or treated. For example, text passages may be medical transcripts, doctor notes, lab reports, excerpts there from, or combinations thereof. The unstructured text passages of the medical record are used.

The labeled text passages relate to a medical concept or concepts. The goal is to deduce if a patient satisfies certain medical concept, C, given text passages from medical records D for a patient. Example medical concepts could be 'Congestive Heart Failure', 'Cardiomyopathy', or 'Any Intervention.' The outcome of this analysis will be at the sentence, paragraph, document, or patient file level. For example, the probability that a document indicates that the medical concept or concepts of interest are satisfied ('True') or not ('False') is modeled. The model may be based on one level (e.g., sentence) for determining the state at a higher or more comprehensive level (e.g., paragraph, document, or patient record). The state space is Boolean (e.g., true or false) or any discrete set of three or more options (e.g., large, medium and small). Boolean states spaces may be augmented with the neutral state (here referred to as the 'Unknown' state).

In one embodiment, the training data is a set of sentences S labeled 'True', 'False' or 'Unknown' to signify if a particular sentence positively asserts the presence of the medical concept, positively asserts the absence of the medical concept, or does not say anything about the medical concept, respectively. This approach does not classify documents directly. Instead, the text passage unit of inference is the sentence. The sentences within a document are analyzed and the results of the sentence level analysis may be used at the document level. Optionally, the dataset can include documents or other levels of text passages labeled for the criteria of interest.

The following notation is used herein, but other notations may be used. C is a random variable denoting the text passage label (e.g., C is the medical concept). D is a number of text passages and/or patients. N is the number of text passages in a larger text passage (e.g., N sentences in a document, or N documents in a patient record). $Y_i$ is a random variable denoting the text passage level being modeled, such as the sentence label. The subscript i is for the i-th text passage (e.g., i-th sentence in a document). $X_i^*$ is a vector of words for a given text passage Y. For example, $X_{ij}$ denotes the j-th word in the i-th sentence in a document.

In act 22, words or phrases to be included within the probabilistic model are determined. In one embodiment, all words or phrases within the training data are used. In another embodiment, an expert, medical professional, ontology, procedure, guideline or other source provides a list of relevant words or phrases for a given medical concept. The key words X to be used for training the probabilistic model are known or given before learning.

In another embodiment, a processor determines the set of words or phrases. Mutual information (MI) criteria processing is performed to learn the most relevant or determinative words or phrases. These relevant words X for a medical concept are automatically determined. The medical concept, such as "Congestive Heart Failure," may be referred to as 'Heart Failure', 'Congestive Heart Failure', 'CHF', or by the New York Heart Association functional class to which it belongs (e.g., "ii"). Mutual information (MI) is a measure based on information theoretical principles employed to determine the relevance of the terms or phrases for each of the medical concepts of interest.

The same or different training data, such as the available labeled sentences, may be used. For example, let the sentence label be the random variable Y, and the words in the sentence be denoted by $X_i$. The most informative word for the condition Y is the one that maximizes the following:

$$\text{argmax}_i(I(Y:X_i)) \quad (16)$$

where I is the mutual information, $$I(Y; X_i) = \sum_y \sum_{x_i} P(y, x_i) \log \frac{P(y, x_i)}{P(y)P(x_i)} \quad (17)$$

The K most informative words are chosen using this criterion. This analysis need not be limited to single words, but can be extended to bigrams, trigrams, or other numbers of words. It is often the case in the medical domain that a condition is stated as a phrase containing multiple words rather than a single word. A set of key terms is determined from single words or combinations of words that maximize the MI measure with respect to each clinical medical concept under consideration. The complexity of the above procedure is proportional to the complexity of building joint probability tables multiplied by the number of words (including bigrams/trigrams) to be considered.

In act 24, a processor constructs a probabilistic model of the medical concept as a function of the labeled text passages of the medical transcripts. The probabilistic model learns statistical distributions of words or phrases relative to the state of the patient. The state may be limited in correspondence with the labeling of the training data, such as the state of the medical concept being limited to true and false, or true, false and unknown.

A medical concept is implied through words or phrases. Every concept has a series of key terms or phrases, which assert the state of the concept. For a concept like 'Congestive Heart Failure', the key terms could be congestive, heart, failure, new, york, association, functional, class, ii, iii, symptoms, cardiomyopathy, nyha, and chf. The terms provide the random variables of interest in the probabilistic model to be trained.

The relationships of the terms among themselves and with the medical concept of interest are learned. The set of conditional independences among the random variables of the model and their quantitative dependencies (i.e., conditional and prior probability functions) are determined.

Figure 2:
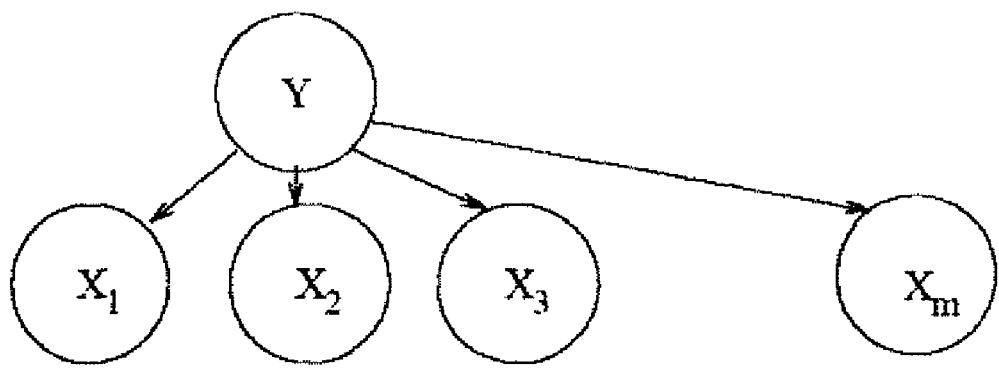
FIG. 2 is a graphical representation of a graphical model according to one embodiment.

In one embodiment, the probabilistic model is represented as a graphical model (e.g., a Bayes network), but other models may be used. Graphical models are a useful formalism for representing and analyzing probability models. A graphical model is a directed acyclic graph, such as shown in FIG. 2, and a set of probability functions. Every node is associated with a random variable and the set of edges or interconnections define their probabilistic dependencies. The probability functions are (1) conditional probabilities relating every node with the node's parents and (2) prior probabilities assigned to every parent-less node. This representation captures the dependencies and conditional independences between the various random variables, describing the probability model.

In FIG. 2, each key term is represented by a node in a graph. The key terms for a given criteria together form a random vector X. The medical concept to be detected is also a random variable, denoted by Y. The conditional probability P(Y|X) is calculated using the training data as constrained by the model.

The network can be arbitrarily complex depending on the complexity of the medical concept of interest. Moreover, the structure of the Bayes net need not be fixed and could be learned. Once the distribution over the text passage labels in a document has been obtained, the label for other levels of text passage may be inferred, such as by probabilistic inference.

The probabilistic model is trained using any now known or later developed machine learning approach. For example, generative or discriminative learning is used. Generative classifiers learn a model of the joint probability P(X, Y), of the word vector X and sentence label Y. The conditional probability of interest is then found using Bayes rule to calculate P(Y|X). Discriminative classifier models learn the conditional P(Y|X) directly (i.e., learn as a direct map from input values to labels). Discriminative learning involves a summation of the order of the number of distinct class labels. The presence of a large number of class labels makes discriminative learning computationally more expensive. Optimal models can be more easily derived in many cases using generative model learning.

Any now known or later developed model may be used. In one embodiment, a Naive Bayes model of clinical terms and patient conditions is constructed. This model makes the modeling assumption that words or terms in a text passage (e.g., sentence) are conditionally independent given their label. FIG. 2 is a graphical representation of a network for this Naïve Bayes model. Different networks may be used, such as multiple layers or hierarchy of words or phrases, interconnections between words or phrases, and different nodal groupings for different medical concepts in a same model. In FIG. 2, Y is the sentence label random variable, and X is the random vector of words used to determine the label, such as the key terms.

To train or learn the probabilistic model, the parameters of the model are estimated. These parameters are $P(x_j|y)$, the conditional probability of a word from the chosen set of words given the label. The parameters of the Bayes network in question also include the prior distribution on Y, P(y) (for every state of Y). In order to infer a state from a trained model, a distribution for y given x is determined (i.e., P(y|x) is calculated). Denote $P(x_k=a, y=b)$ by $\theta^k_{ab}$ where a can take on values 'True' or 'False', and b can take on values 'Unknown', 'True', or 'False'. The priors, P(y=b), are denoted by $\theta_b$. The total number of parameters in the model is (|X|.|Y|)+|Y|−2, where |X| denotes the number of key terms in the vector X and |Y| denotes the number of classes.

In generative learning, the goal is to maximize the joint P(y,x) for the training data. Assuming m words in the vector x, the joint probability is represented as:

$$P(y, x) = P(x | y)P(y) \quad (1)$$
$$= P(y) \prod_{j=1}^{m} P(x_j | y)$$

Under the Naive Bayes assumption, learning amounts to a count of frequencies of $x_j$ under different values for y, given fully observed data. Generative learning for the above model amounts to setting the parameter to the following frequency counts:

$$\theta_{ab}^k = \frac{\sum_{i=1}^{N} \delta(x_{ik} = a)\delta(y_i = b)}{N} \quad (3)$$

$$\theta_b = \frac{\sum_{i=1}^{N} \delta(y_i = b)}{N} \quad (4)$$

In discriminative learning, the conditional P(y|x) is maximized for the training data:

$$P(y \mid x) = \frac{P(x \mid y)P(y)}{P(x)} \quad (2)$$

$$= \frac{P(y)\prod_{j=1}^{m} P(x_j \mid y)}{\sum_y \prod_{j=1}^{m} P(x_j \mid y)P(y)}$$

The marginal, P(x), in the denominator makes parameter estimation more involved, since the marginal requires a summing over the various states of the label y. For a small number of states (e.g., true/false/unknown), discriminative learning is less computationally expensive than for a larger number of states.

In discriminative learning, the (log) conditional likelihood, F, may be maximized:

$$F = \log P(Y \mid X) \quad (5)$$

The constraints are:

$$\sum_a \theta_{ab}^k = 1 \quad (6)$$

$$\sum_b \theta_b = 1 \quad (7)$$

Every row of the frequency count matrix sums to a value of 1. For equation (7), a single row is provided as a vector. The following formulation ensures constraints (6) and (7) are satisfied. Define:

$$\theta_{ab}^k = \frac{e^{\alpha_{ab}^k}}{\sum_a e^{\alpha_{ab}^k}} \quad (8)$$

$$\theta_b = \frac{e^{\alpha_b}}{\sum_b e^{\alpha_b}} \quad (9)$$

By taking the partial derivative of equation (2) with respect to each component of α, the following equation results:

$$\frac{\partial F}{\partial \alpha_{ab}^k} = \begin{cases} \sum_{i=1}^{N} \delta(y_i = b)(\theta_{ab}^k[1 - P(y_i \mid x_i)] - [1 - P(y_i \mid x_i)]) & \text{when } x_{ik} = a \\ \sum_{i=1}^{N} \delta(y_i = b)(\theta_{ab}^k[1 - P(y_i \mid x_i)]) & \text{when } x_{ik} \neq a \end{cases} \quad (10)$$

$$\frac{\partial F}{\partial \alpha_b} = \sum_{i=1}^{N} \delta(y_i = b) - \sum_{i=1}^{N} P(y_i = b \mid x_i) \quad (11)$$

where, $$P(y_i = b \mid x_i) = \frac{\prod_{j=1}^{m} P(x_{ij} \mid y_i = b)P(y_i = b)}{P(x_i)} \quad (12)$$

On simplifying the derivative of equation (10), the following is provided:

$$\theta_{ab}^k = \frac{\sum_{i=1}^{N} \delta(x_{ik} = a)\delta(y_i = b)[1 - P(y_i \mid x_i)]}{\sum_{i=1}^{N} \delta(y_i = b)[1 - P(y_i \mid x_i)]} \quad (13)$$

At the algorithmic level, since neither equation (13) nor equation (11) yield a close form solution for all parameters, parameter updates are performed iteratively in the direction of the gradient using equations (13) or (11). The gradient is the direction of maximum rate of increase in the value of the function.

Figure 3:
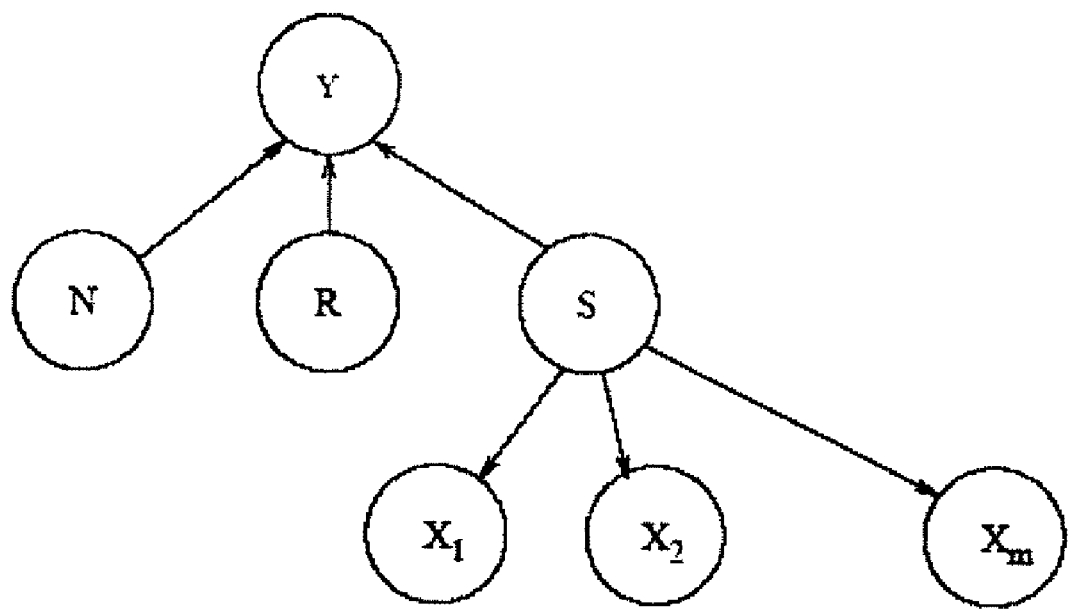
FIG. 3 is a graphical representation of a graphical model according to another embodiment.

In another model embodiment, the Bayes model uses different word groupings. FIG. 3 shows one example where a summary node for the text passage, a negation node, and a modifier node are provided. Some terms or words are treated differently than or separately from others, as represented by the three different types—summary, negation and modifier. In the Naive Bayes setting of FIG. 2, statistical independence between the various features is assumed In text processing, this assumption is referred to as the bag of words model for document classification The occurrence of one word is considered independent of the occurrence of other words given the label of the document. For more complex word-word-label dependencies occurring in text, a different graphical model may be used. Other models than shown in FIG. 3 may be used, such as without separate modifier or negation nodes or with additional nodes or levels.

The random variables N and R represent the presence or absence of negation (N) and modifier (R) terms. These words are predefined. For example, a programmer or other resource provides a list of negation terms and another list of modifier terms, such as derived from a dictionary. Negation terms may include no, never, deny, impossible, other negative words, or derivations thereof. Modifier terms may be adjectives, probabilistic terms (e.g., about, likely, possible, maybe or others), derivations thereof, or combinations thereof. The negation and/or modifier terms may be identified in act 22, such as using mutual information criteria. Other sets or groupings of words than N and R can be used.

The summary node (S) represents the presence or absence of the criteria, and is assumed to be observed during training but not at the time of inference. The input words are used to determine the summary node information at the time of inference. The vector of words X is formed by words or terms that are relevant to the condition Y, such as key terms. The vector X does not include the negation or modifier terms, but may in alternative embodiments. The negation (N), the modifiers (R), and the group of key terms (S) are no longer independent given the label. Because of the increased model complexity, the nodes allow for modeling higher-level dependencies between words and the criteria of interest Y.

The network of FIG. 3 can be trained discriminatively or generatively. Discriminative learning can be effectively done in two steps. First, the parameters $P(x_j|s)$ are learned for all the values in the domain of $X_j$ and S. This learning is the same or different than training the model of FIG. 2 (i.e., the Naive Bayes network). Second, the conditional probability table $P(y|n,r,x)=\Sigma_s P(y|n,r,s)P(s|x)$ is learned. This second learning stage uses discriminative learning in this model and marginalizes over the unobserved s. The most likely value of Y is chosen as the inferred label if only one value of Y is to be given as answer.

Where the probabilistic model is trained from text passages at one level, the model may be extended to other levels of the text passages. For example, the probabilistic model is trained with sentence-level labeling. For document-level labeling, the labels of the different sentences are assumed to be independent of each other given the label of the document. The document label random variable can take on the values in the set ('True', 'False') for the medical concept. For either model approach, a posterior distribution over c can be computed as follows:

$$P(c | x_1 \ldots i \ldots N) = \prod_{i=1}^{N} \left( \sum_{y_i} P(c | y_i) P(y_i | x_i) \right) \quad (14)$$

$$= \prod_{i=1}^{N} \left( \sum_{y_i} \left[ \frac{P(y_i | c) P(c) P(y_i | x_i)}{\sum_{\hat{c}} P(y_i | \hat{c}) P(\hat{c})} \right] \right) \quad (15)$$

For the model of FIG. 3, X is replaced by X, N, and R. Other derivations may be used, such as median occurrence of component text passages.

The probabilistic model may include other sources of information. For example, the probabilistic model is trained using the unstructured text passages, and unstructured image information and/or structured data (e.g., test results, laboratory values, patient demographics, billing codes).

In act 26 of FIG. 1, the probabilistic model is output. For example, the probability distributions, matrices, and/or frequency counts determined in act 24 are output. The output may be used by software or other processing for application and/or analysis of the probabilistic model.

The output is to a display, to a printer, to a computer readable media (memory), or over a communications link (e.g., transfer in a network). The probabilistic model may be output for use by the same or different processor for applying the model in act 28. The output defines, describes or represents the probabilistic model constructed with the training data.

The output may include additional information. For example, the training data used to train the model is identified or also provided. As another example, the medical concept or concepts applicable to the model are identified. The key terms or other information used to construct the model may be identified.

In act 28, the probabilistic model is applied. The probabilistic model is applied to a medical transcript or transcripts of one or more patients. The model is incorporated onto a computer, such as into hardware, software, or both. The incorporation allows application of the probabilistic model to an unlabeled, text passage for a patient. The text passage provides values (e.g., term found or not found) for a specific or individual text passage. The model is applied to the individual patient information to output a state or previous state of a specific patient.

The text passage is input for application of the probability model. The data is input manually, such as typing in the text passage. Alternatively, the data is mined from a stored file. The text passage may be identified as a file or from part of a file, such as loading a text file without header or other word processing codes.

The probabilistic model probabilistically associates different words of the medical transcript to a state of the medical concept. For example, conditional and prior probability functions of words or phrases relative to the state are used. The application may be of a discrimitively learnt model or other model. For example, the model represented by FIG. 3 (i.e., a Bayes model having a summary node for the text passage, a negation node, and a modifier node) is applied. The most likely state of the medical concept is estimated based on the patient specific textual information. The estimation is performed by applying the existence or not of key terms, and modeling the contribution of the existing terms to the probability of one of the states of the medical condition. The probability model determines an outcome, such as a state. The relative probabilities of different states may be determined.

In this approach, there is no need to manually specify rules (for example phrase spotting rules), but manually built rules may be incorporated with the learned probabilities. Training from the labeled text can reduce the time needed to represent medical concepts. The human effort needed to manually build rules may be considerable. Thus, the present approach is closer to fully automatic learning of medical concepts. The probabilistic model trained from labeled text may be applied to patient medical transcripts for the medical concept of interest with less manual rule creation.

In act 30, the state of the medical concept, as reflected in the text passage, is output. The state indicated by the medical transcript is displayed, stored, or transferred for use in diagnosis or other purposes. The state is a function of the probabilistic associations of the different words to the state.

Other information may be output, such as the probability determined for the state, a probability distribution, or state for different levels of text passages (e.g., state for a sentence, state for a document, and state for a patient file).

In the following experiments, REMIND™ was used to label training data. In these experiments, REMIND was configured as an end-to-end system that uses hand-coded rules and 'Phrase Spotting' to detect disease conditions from doctors' notes. REMIND is disclosed in U.S. Published Application No. 2003/0120458, the disclosure of which is incorporated herein by reference. Other methods can be used for labeling training data (e.g., from trained person). The rules were written with the help of an expert. Within each document, the sentences that matched the rules were labeled by REMIND. Regarding document labeling, for each medical concept, documents were labeled according to the prevailing state of the concept (a simple winner-takes-all approach). The training set consisted of 3142 documents labeled 'True' or 'False' for each of 7 concepts (the sentences within a document were labeled 'True', 'False' or 'Unknown' for the condition). The test set included of 3137 documents.

Using mutual information criteria as the measure of informativeness of words, a list of words was obtained for each condition. Any number of words was chosen for each medical concept as key terms. The example medical concepts and some examples of the automatically determined key terms include:

CHF: congestive, heart, failure, new, york, association, functional, class, ii, iii, symptoms, cardiomyopathy, nyha, and chf;

Cardiomyopathy: ischemic, cardiomyopathy, ejection, fraction, history, heart, improvement, program, follow, up, echocardiogram, impression, recent, most, and york;

Cardiac perforation: pericardial, effusion, shunt, thrombus, noted, intracardiac, history, present, illness, masses, tumors, coronary, artery, disease, and echocardiographic;

Revascularization: coronary, artery, bypass, disease, graft, status, post, right, left, anterior, descending, history, grafting, and internal;

CHFSymptoms: pain, shortness, breath, chest, coronary, artery, disease, paroxysmal, nocturnal, dyspnea, and orthopnea;

Intervention: coronary, artery, bypass, disease, graft, status, post, right, left, anterior, descending, history, grafting, and internal;

Stenosis: right, coronary, artery, stenosis, left, anterior, descending, mid, internal, mammary, and disease;

Negation terms and modifiers were manually determined using a dictionary. For example, the list of negation terms included: no, never, not, non, negative, neither, denies, deny, didn't, doesn't, don't, hadn't, hasn't. The list of modifier terms included: mild, moderate, suspect, suggestive, may, might, could, potential, potentially, indicative. Different, fewer, or additional terms may be included in either list.

Performance experiments were conducted under three different settings. In a first setting, the Naive Bayes (the first model as shown in FIG. 2) was trained discriminatively (referred to as ND). In a second setting, another Bayes Net (the second model as shown in FIG. 3) was used with the summary node, S, trained generatively (referred to as IG). In a third setting, the same model as shown in FIG. 3 was used, but the summary node, S, was trained discriminatively (referred to as ID). Table 1 gives a performance comparison of the three models.

TABLE 1

Document level performance comparison of the 3 models for 7 conditions TP = True Positive FP = False Positive TN = True Negative FN = False Negative

| | Naive Discriminative | | | | Complex Generative | | | | Complex Discriminative | | | |
|---|---|---|---|---|---|---|---|---|---|---|---|---|
| | TP | FP | TN | FN | TP | FP | TN | FN | TP | FP | TN | FN |
| CHF | 289 | 59 | 2466 | 323 | 591 | 61 | 2464 | 21 | 589 | 49 | 2476 | 23 |
| Cardiomyopathy | 107 | 134 | 2046 | 850 | 949 | 11 | 2169 | 8 | 949 | 8 | 2172 | 8 |
| Cardiac Perforation | 0 | 46 | 3075 | 19 | 15 | 31 | 3090 | 4 | 15 | 31 | 3090 | 4 |
| Revascularization | 1026 | 116 | 1809 | 188 | 1140 | 319 | 1606 | 74 | 1128 | 274 | 1651 | 86 |
| CHF Symptoms | 523 | 106 | 2217 | 294 | 625 | 86 | 2237 | 192 | 601 | 58 | 2265 | 216 |
| Intervention | 909 | 177 | 1872 | 181 | 996 | 389 | 1660 | 94 | 982 | 344 | 1705 | 108 |
| Stenosis | 99 | 216 | 2790 | 33 | 112 | 400 | 2606 | 20 | 110 | 351 | 2655 | 22 |

TABLE 2

Sensitivity and Specificity of the three models

| | Naive Discriminative | | Complex Generative | | Complex Discriminative | |
|---|---|---|---|---|---|---|
| | Sensitivity | Specificity | Sensitivity | Specificity | Sensitivity | Specificity |
| CHF | 52.78 | 97.66 | 96.57 | 97.58 | 96.24 | 98.05 |
| Cardiomyopathy | 11.18 | 93.85 | 99.16 | 99.49 | 99.16 | 99.63 |
| Cardiac Perforation | 0 | 98.52 | 78.94 | 99.00 | 78.94 | 99.00 |
| Revascularization | 84.51 | 93.97 | 93.90 | 83.42 | 92.91 | 85.76 |
| CHF Symptoms | 64.01 | 95.43 | 76.49 | 96.29 | 73.56 | 97.50 |
| Intervention | 83.39 | 91.36 | 91.37 | 81.01 | 90.09 | 83.21 |
| Stenosis | 75 | 92.81 | 84.84 | 86.69 | 83.33 | 88.32 |

Figure 4:
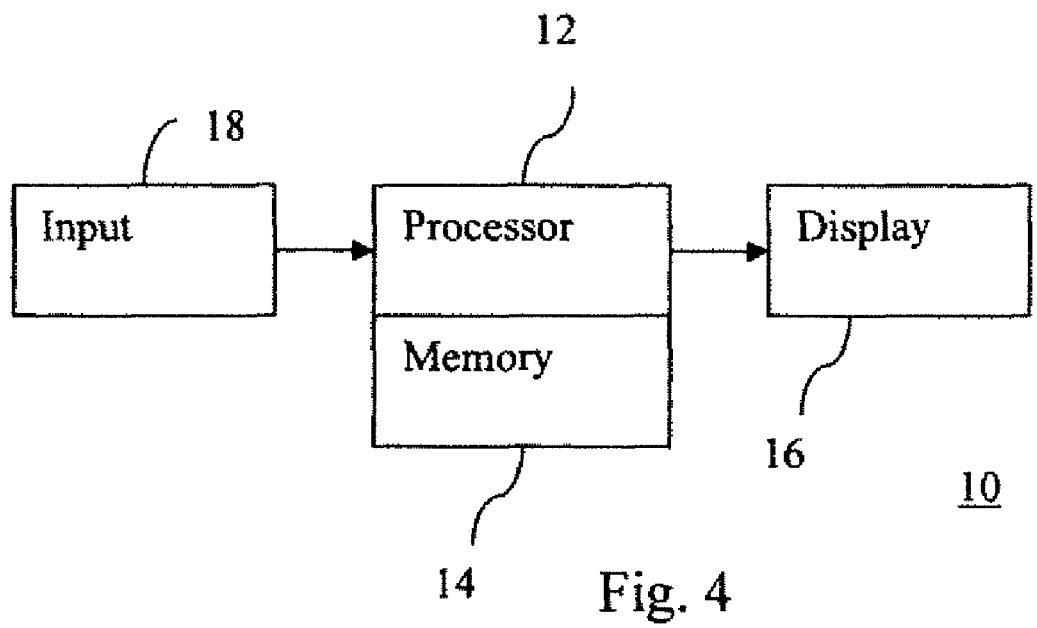
FIG. 4 is a block diagram of one embodiment of a system for learning about and inferring a medical concept from a medical transcript.

FIG. 4 shows a block diagram of an example system 10 for inferring a medical concept from a medical transcript. The same or different system 10 may be used for machine learning of the probabilistic model from labeled text passages.

The system 10 is a hardware device, but may be implemented in various forms of hardware, software, firmware, special purpose processors, or a combination thereof. Some embodiments are implemented in software as a program tangibly embodied on a program storage device. The system 10 is a computer, personal computer, server, PACs workstation, imaging system, medical system, network processor, network, or other now know or later developed processing system. The system 10 includes at least one processor (hereinafter processor) 12 operatively coupled to other components. The processor 12 is implemented on a computer platform having hardware components. The other components include a memory 14, a network interface, an external storage, an input/output interface, a display 16, and a user input 18. Additional, different, or fewer components may be provided.

The computer platform also includes an operating system and microinstruction code. The various processes, methods, acts, and functions described herein may be part of the microinstruction code or part of a program (or combination thereof) which is executed via the operating system.

The processor 12 receives or loads medical transcript information. The medical transcript is a text passage, such as unstructured, natural language information from a medical professional. Unstructured information may include ASCII text strings, image information in DICOM (Digital Imaging and Communication in Medicine) format, or text documents. The text passage is a sentence, group of sentences, paragraph, group of paragraphs, document, group of documents, or combinations thereof.

The text passage is for a patient. Text passages for multiple patients may be used. The state of the patient related to one or more medical concepts is determined from the text passage. Multiple states for a respective multiple medical concepts may be determined for a given text passage. Alternatively, the most probable medical concept and corresponding state are identified.

The user input 18, network interface, or external storage may operate as an input operable to receive user identification of the medical transcript. For example, the user enters the text passage by typing on a keyboard. As another example, a stored file in a database is selected in response to user input. In alternative embodiments, the processor 12 automatically processes text passages, such as identifying any newly entered text passages and processing them.

The user input 18 is a mouse, keyboard, track ball, touch screen, joystick, touch pad, buttons, knobs, sliders, combinations thereof, or other now known or later developed input device. The user input 18 operates as part of a user interface. For example, one or more buttons are displayed on the display 16. The user input 18 is used to control a pointer for selection and activation of the functions associated with the buttons. Alternatively, hard coded or fixed buttons may be used.

The processor 12 has any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor 12. The processor 12 implements the program alone or includes multiple processors in a network or system for parallel or sequential processing.

The processor 102 performs the workflows, machine learning, model training, model application, and/or other processes described herein. For example, the processor 12 or a different processor is operable to extract terms for use in modeling, learn a probabilistic model, and apply the trained probabilistic model. For applying the model, the model may have been trained by a different processor or the same processor 12.

For application of the probabilistic model, the processor 12 receives a text passage from a medical transcript. The probabilistic model is applied to the text passage of the medical transcript. Key terms are identified in the text passage, such as identifying a discrete set of terms as elements identified as a function of mutual information criteria. The key terms are associated with learned statistics of words or phrases relative to the state of the medical concept of interest. Based on the statistics for conditional and prior probability functions of words or phrases relative to the state or a discrimitively-learnt model, a state with a highest probability given the terms identified in the text passage is determined. In one embodiment, negation and/or modifier terms are identified and input to the model separately from the key terms of a medical concept. A Bayes or other model has a summary node for the text passage, a negation node, and a modifier node. The state is inferred as a function of an output from the probabilistic model applied to the text passage.

Based on the application of the probabilistic model, the processor 102 outputs a state. The state may be a most likely state. A plurality of states associated with different medical concepts may be output. A probability associated with the most likely state may be output. A probability distribution of likelihoods of the different possible states may be output.

The processor 12 outputs the state and/or associated information on the display 16, into a memory, over a network, to a printer, or in another media. The display is text, graphical, or other display.

The display 16 is a CRT, LCD, plasma, projector, monitor, printer, or other output device for showing data. The display 16 is operable to output to a user a state associated with a patient. The state provides an indication of whether a medical concept is indicated in the medical transcript. The state may be whether a disease, condition, symptom, or test result is indicated. In one embodiment, the state is limited to true and false, or true, false and unknown. In other embodiments, the state may be a level of a range of levels or other non-Boolean state.

The processor 12 operates pursuant to instructions. The instructions and/or patient records for training a probabilistic model or for inferring a medical concept from a medical transcript are stored in a computer readable memory 14, such as an external storage, ROM, and/or RAM. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The same or different computer readable media may be used for the instructions, the individual patient text passages, and the labeled text passages (training data). The patient records are stored in the external storage, but may be in other memories. The external storage may be implemented using a database management system (DBMS) managed by the processor 12 and residing on a memory, such as a hard disk, RAM, or removable media. Alternatively, the storage is internal to the processor 12 (e.g. cache). The external storage may be implemented on one or more additional computer systems. For example, the external storage may include a data warehouse system residing on a separate computer system, a PACS system, or any other now known or later developed hospital, medical institution, medical office, testing facility, pharmacy or other medical patient record storage system. The external storage, an internal storage, other computer readable media, or combinations thereof store data for at least one patient record for a patient. The patient record data may be distributed among multiple storage devices.

The output state classifies the medical concepts associated with medical text. The classification is used as a second opinion or to otherwise assist medical professionals in diagnosis. In other embodiments, the state of the medical concept is used for quality adherence (see U.S. Published Application No. 2003/0125985), compliance (see U.S. Published Application No. 2003/0125984), clinical trial qualification (see U.S. Published Application No. 2003/0130871), billing (see U.S. Published Application No. 2004/0172297), and improvements (see U.S. Published Application No. 2006/0265253). The disclosures of these published applications referenced above are incorporated herein by reference.

The application of the model may be run using the Internet. The created probabilistic model may be accessed using the Internet. Additionally, the modeling may be run as a service. For example, several hospitals may participate in the service to have their patient information mined for diagnostic assistance or guideline compliance, and the text passage information may be stored in a data warehouse owned by the service provider. The service may be performed by a third party service provider (i.e., an entity not associated with the hospitals). Based on a per-use license, a periodically paid license, or other payment, the state output by the model may be compared or otherwise made available for verifying information.

The key terms, medical concepts, states, or training data may be changed for a given application. For example, the probabilistic model may be different for some medical practitioners or institutions. Different key terms may be provided for different groups of medical professionals. Conditional, prior, or other probabilities may be different or altered.

The probabilistic model can be used for active learning. Key terms, states, or other data may be altered or updated, such as based on confirmation or further labeling by an expert.

Various improvements described herein may be used together or separately. Any form of data mining or searching may be used. Although illustrative embodiments have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for inferring a medical concept from a medical transcript, the system comprising:
    an input operable to receive user identification of the medical transcript;
    a processor operable to receive a text passage from the medical transcript and operable to apply a probabilistic model to the text passage of the medical transcript, the probabilistic model trained as a function of a discrete set of words or phrases, wherein the probabilistic model comprises a Bayes model having a summary node representing the presence or absence of at least one medical concept and observed during training but not at the time of inference for the text passage, a negation node, and a modifier node, the constructing comprising a function of discriminative learning; and
    a display operable to output a state associated with a patient, the state being inferred as a function of an output from the probabilistic model applied to the text passage.

2. The system of claim 1 wherein the state is a disease, condition, symptom, or test result, the state being limited to true and false, or true, false and unknown.

3. The system of claim 1 wherein the medical transcript comprises unstructured, natural language information from a medical professional.

4. The system of claim 1 wherein the output from the probabilistic model comprises an indication of whether a medical concept is indicated in the medical transcript.

5. The system of claim 1 wherein the probabilistic model comprises learned statistics of words or phrases relative to the state.

6. The system of claim 1 wherein the probabilistic model includes probabilities associated with images, structured data, or combinations thereof.

7. The system of claim 1 wherein the probabilistic model comprises conditional and prior probability functions of words or phrases relative to the state.

8. The system of claim 1 wherein the words or phrases included within the discrete set are learned as a function of mutual information.

9. In a computer readable storage medium having stored therein data representing instructions executable by a programmed processor for inferring a medical concept from a medical transcript, the instructions comprising:
    applying a probabilistic model to the medical transcript of a patient, the probabilistic model probabilistically associating different words of the medical transcript to a state of the medical concept, wherein the probabilistic model comprises a Bayes model having a summary node representing the presence or absence of at least one medical concept and observed during training but not at the time of inference for the text passage, a negation node, and a modifier node, the constructing comprising a function of discriminative learning; and
    outputting the state as indicated by the medical transcript of the medical concept as a function of the probabilistic associations of the different words to the state.

10. The instructions of claim 9 wherein the probabilistic model comprises conditional and prior probability functions of words or phrases relative to the state.

11. A method for learning about a medical concept from a medical transcript, the method comprising:

receiving a plurality of labeled text passages from medical transcripts;

constructing, with a processor, a probabilistic model of the medical concept as a function of the labeled text passages of the medical transcripts, the constructing being a function of discriminative learning; and outputting the probabilistic model;

wherein constructing the probabilistic model comprises learning with a Bayes model having a summary node representing the presence or absence of at least one medical concept and observed during training but not at the time of inference for the text passage, a negation node, and a modifier node.

12. The method of claim 11 wherein the medical transcripts comprise unstructured, natural language information from a medical professional, and wherein a state of the medical concept is limited to true and false, or true, false and unknown.

13. The method of claim 11 wherein construction comprises learning, with the processor, statistical distributions of words or phrases relative to a state of the medical concept.

14. The method of claim 11 further comprising determining, with the processor, words or phrases to be included within the probabilistic model, the determining being learned as a function of mutual information.

15. The method of claim 11 wherein constructing comprises learning conditional and prior probability functions of words or phrases relative to a state of the medical concept.

* * * * *